(12) United States Patent
Dorn

(10) Patent No.: US 6,558,371 B2
(45) Date of Patent: May 6, 2003

(54) APPARATUS FOR HOLDING A TROCAR SLEEVE IN DIFFERENT SPATIAL ORIENTATIONS

(75) Inventor: Jürgen Dorn, Neulussheim (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 0 days.

(21) Appl. No.: 09/908,959

(22) Filed: Jul. 19, 2001

(65) Prior Publication Data

US 2002/0019639 A1 Feb. 14, 2002

Related U.S. Application Data

(63) Continuation of application No. PCT/EP00/00309, filed on Jan. 17, 2000.

(30) Foreign Application Priority Data

Jan. 20, 1999 (DE) .......................................... 199 02 036

(51) Int. Cl.[7] .............................................. A61B 17/00
(52) U.S. Cl. ........................ 606/1; 604/513; 604/539; 600/206
(58) Field of Search ........................... 606/1, 108, 130; 604/513, 264, 539; 600/204, 206, 207, 208, 114, 115

(56) References Cited

U.S. PATENT DOCUMENTS

| | | | | |
|---|---|---|---|---|
| 5,279,575 A | * | 1/1994 | Sugarbaker | 604/104 |
| 5,281,232 A | * | 1/1994 | Hamilton et al. | 600/130 |
| 5,658,272 A | * | 8/1997 | Hasson | 606/1 |
| 6,267,769 B1 | * | 7/2001 | Truwit | 606/1 |

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A holding apparatus is provided for a trocar sleeve suitable for fixing the trocar sleeve in different positions relative to the patient. The holding apparatus comprises a base member fixedly positionable with respect to the patient and a retainer for the trocar sleeve. The retainer is connected to be tiltable with respect to the base member by a flexible connecting member. According to the invention, the connecting member has a first flexible operational state and a second rigid operational state and the connecting member can be switched between the first flexible and the second rigid operational state.

22 Claims, 5 Drawing Sheets

APPARATUS FOR HOLDING A TROCAR SLEEVE IN DIFFERENT SPATIAL ORIENTATIONS

CROSSREFERENCE OF PENDING APPLICATION

This application is a continuation of pending international application PCT/EP 00/00309 filed on Jan. 17, 2000 and designating U.S.

BACKGROUND OF THE INVENTION

The present invention relates to an apparatus for holding a trocar sleeve in different spatial orientations relative to a patient, comprising a base member fixedly positionable relative to the patient and a retainer for the trocar sleeve, where the retainer is connected to be tiltable with respect to the base member by a flexible connecting member.

A holding apparatus of this type is disclosed in U.S. Pat. No. 5,540,675.

A trocar provides access into the body in minimally invasive surgery. A small incision can be made with a trocar mandrel, through which incision the trocar sleeve is inserted into the body of the patient. The trocar mandrel is subsequently withdrawn from the trocar sleeve. The trocar sleeve thus forms an access channel into the body of the patient.

Trocars are used particularly in minimally invasive surgeries in the stomach region, the field of laparoscopy. Its use however is not limited thereto. Medical instruments can be reliably guided and held in the channel formed by the trocar sleeve and, in addition, the channel serves to supply or discharge fluids or gases into or out of the patient's body. For this purpose, a flap valve housing is usually provided at the proximal end of the trocar sleeve with corresponding sealings and stop cocks.

The trocar sleeve is located in a spatial orientation corresponding to the incision channel. The trocar sleeve however can be varied in its orientation by hand; it returns to the direction of the incision channel when the tube is released. This results from the tendancy of the tissue layers penetrated by the trocar to realign themselves to a certain position. For this reason, apparatus of the above-mentioned type are used to hold the trocar sleeve in certain positions.

One or more different spatial orientations of the trocar sleeve is desirable during a surgery. In a first operational state, the holding apparatus retaining the trocar sleeve is slightly adjustable. Once the trocar sleeve is oriented in the desired position, it should no longer change its disposition. In a second operational state, the holding apparatus is rigid and the trocar sleeve remains fixed in the selected spatial orientation.

The holding apparatus disclosed in mentioned U.S. Pat. No. 5,540,675 comprises an annular base portion which is directly secured to the patient's body with an adhesive layer. The annular base portion is connected with elastic, rubber connecting members to a retainer arranged centrally with respect to the base portion and in the starting condition perpendicular to it. The retainer in the present case itself is tube-shaped. The trocar sleeve is inserted into the retainer. To orient and to fix the retainer in different directions with respect to the base portion, a telescopic-like tensioning mechanism is provided consisting of at least one tensioning element adjustable in length. It is secured between the radially outward region of the base portion and the end of the retainer lying remote from the base portion. The inclination of the retainer relative to the base portion can be varied by adjusting the length of the tensioning element. However, it is first necessary to release the tensioning element with a screw, to adjust the tensioning element to the desired length and finally to again tighten the screw. In one embodiment of the known holding apparatus, three tensioning elements in the form of a tripod are arranged about the retainer for reasons of stability. The trocar sleeve can only be tilted in one single plane with one tensioning element. The adjustment and securement of the desired position of the retainer is complicated in this known holding apparatus. To change the spatial position of the trocar sleeve, all three tensioning elements for fixing the retainer must first be released, and then adjusted and finally retightened. Should the operator after inserting an instrument, for example an endoscope, find that the orientation is not yet exact, he must again carry out the complicated procedure. Extremely tilted positions of the trocar sleeve are not achievable in a stable manner due to the tripod geometry.

Furthermore, the tensioning elements of this known apparatus comprise numerous bacterial niches, cavities and corners, for example the threadings of the adjustable screws and the telescopic shafts, so that the known apparatus is difficult to clean and to sterilize.

Another type of apparatus for aligning and fixing medical instruments is described in the U.S. Pat. No. 5,597,146, which is representative for numerous similar arrangements. This type of apparatus comprises a multi-link pivot arm, whose individual link elements can be oriented independent from one another about different axes. A medical instrument to be fixed can be positioned and held at an arbitrary position, similar to a robot arm. This type of apparatus however is very complicated with respect to its construction and manufacture. In addition, it takes up space on the operating table above the patient and thus obstructs the surgeon's access to the patient from several directions.

It is, therefore, object of the present invention to provide an apparatus of the mentioned type, which is simple to operate and enables a rapid and at the same time reliable adjustment and fixation of the spatial orientation of the trocar sleeve relative to a patient.

SUMMARY OF THE INVENTION

This object is achieved in that the connecting member has a first operational state in which it is flexible and a second operational state in which it is rigid and in that the connecting member is switchable between the first flexible and the second rigid operational state.

The apparatus according to the invention does not require telescopic-like or column-like tensioning elements held with screws, whose handling is cumbersome and complicated. The invention instead provides the degree of flexibility or of rigidity of the flexible connecting member to be variable itself. It is therefore possible in a first operational state, where the connecting member is flexible, to align the trocar sleeve and also the medical instrument therein in the desired position. By switching over to the second operational state where the connecting member is rigid, the trocar sleeve is then fixed in the adjusted position.

The realization of a connecting member with two such different operational states is technically possible in different ways. Preferred manners of realization are correspondingly described in the following with reference to the dependent claims.

The apparatus according to the present invention has the advantage that the adjustment and fixation of the trocar sleeve position and therefore the medical instrument passed therethrough, is easily possible in any, even extreme tilted position in the first flexible operational state, while the adjusted position is safely and reliably held in the second rigid operational state. Compared to the known apparatus, the present apparatus is much easier to operate. At the same time, it is possible to place the present apparatus with its base directly adjacent to the patient to be treated, for example on his abdominal wall. This has the advantage that the apparatus and therefore the trocar sleeve held therein follows changes in the position of the patient. An undesired relative movement of the trocar sleeve with respect to the patient is avoided. Finally, the present apparatus requires very little space, so that access to the patient from different sides is not obstructed.

The connecting member comprises an elastic casing filled with a material having variable rigidity. This feature has the advantage that the material can have the properties of a flowable mass in the first operational state, because the material is contained by the elastic casing. With this, a particularly simple adjustment of a given spatial orientation of the trocar sleeve is possible. Furthermore, this feature has the advantage that the apparatus has a uniform and smooth surface, due to the elastic cover, preferably of silicone, which is simple to clean and to sterilize. In the second operational state, the rigid mass then holds the trocar sleeve fixed in the desired spatial orientation.

In a further configuration, the material is a particulate material and the apparatus comprises means for generating a vacuum within the casing. In this configuration, the connecting member of the present apparatus is comparable to a balloon filled with a sand-like material. As long as the balloon casing additionally contains air or another gas, the material in the interior is formable. Correspondingly, this is the first operational state in which the connecting member is flexible.

By creating a vacuum in the casing, the air is suctioned out of the balloon, the particles are pressed against one another and the material loses its formability. The connecting member is rigid in this second operational state. The mentioned feature therefore represents a very simple technical possibility of realizing a connecting member where the operational states according to the present invention.

Furthermore, this embodiment has the advantage that the switching between the first flexible and the second rigid operational state is very rapid and simple with the aid of a valve and a pump. In addition, the necessary means for generating a vacuum are known per se in the field of clinical instruments and are also employed there. The present apparatus thus can be realized particularly inexpensively as a supplement to existing devices. A further advantage of this configuration is that the switching between the first flexible and the second rigid operational state is possible "simply by pushing a button" and if desired can be completely automated.

In a further embodiment, the surface of the particles of the material is configured such that the particles in the closely compressed condition are prevented from sliding past one another and therefore form a rigid mass. This is particularly the case when the particles have edges, so that the individual particles lie immovably upon one another or catch within one another in the pressed form. The feature has the advantage that a particularly high rigidity of the connecting member is achieved in the second operational state.

In a further embodiment, the material with adjustable rigidity is a fluid whose viscosity is adjustable between being elastic and rigid. Such materials are known per se in the prior art. They have a molecular structure where the molecules in different operational states are varyingly strongly coupled to one another and/or oriented with respect to one another. This leads to the fact that the fluids have differing viscosities in different operational states. This feature has the advantage that a very simple and fast reacting possibility is given to realize a connecting member according to the invention with the desired operational states.

In a further embodiment, the viscosity of the material is adjustable in response to an electric and/or magnetic field. These are electric or magnetic viscous fluids, whose molecular structure changes under the influence of the mentioned fields. Alternatively, fluids are known whose viscosity changes depending on pressure. This has the advantage that switching between the operational states according to the invention is very simple and "occurs practically by pushing a button" or when needed can be completely automated.

In a further embodiment of the apparatus, the connecting member comprises a material, which is flexible at a first adjustable operational temperature and is rigid at a second operational temperature. Preferably, the second operational temperature is room temperature, where the present apparatus is normally used. The mentioned feature represents a further, alternative possibility of realizing an apparatus with the connecting member according to the invention.

In a further embodiment, the connecting member is a torus-shaped body with the retainer being arranged in its opening. The feature has the advantage that the connecting member is arranged to surround the retainer and thus guarantees a flexibility or rigidity uniformly in all directions. In addition, a particularly high stability of the apparatus is achieved in the second operational state.

In a further embodiment, the base member is secured to a support frame, which can be adjustably and fixedly mounted to an operating table.

Alternatively, it is also contemplated to fix the present apparatus directly on the patient's body, either alone through its own weight or additionally by using a releasable adhesive. The former feature however has the advantage that the base and thus the entire apparatus can be held substantially more stable and secure with respect to the patient. It is insured that the apparatus is not inadvertently shifted through movements of the patient. At the same time it is ensured that the apparatus can always be positioned optimally with respect to the patient due to the adjustable, but fixed mounting on the operating table.

In a further embodiment, the support frame comprises at least one rail extending over the operating table, preferably in about the transverse direction with respect to the patient. The feature has the advantage that particularly good stability is achieved without the apparatus requiring too much space and obstructing access to the patient. In addition, such a rail can be arranged in simple manner such that the base member of the apparatus lies practically directly on the patient's body, where relative movement between the trocar sleeve and the patient is substantially excluded.

In a further embodiment, the base member is secured to the rail to be slidable. The feature has the advantage that the holding apparatus can be adjusted rapidly and in simple manner, and thus can always be disposed at the optimal position with respect to the patient.

In a further embodiment, the at least one rail along the operating table is shiftable and/or pivotal about a pivot point.

These features also contribute to enhancing the possibilities of use and the positioning capability of the present apparatus. At the same time, the operation of the apparatus is very simple and the apparatus does not represent an obstacle for access to the patient. Furthermore, compared to the variably adjustable, multi-link pivot arm, the embodiment is simple and inexpensive in construction and manufacture. In a further embodiment, the support frame comprises several rails, on which several base members with retainers and connecting members are secured. The advantage is that the stability of the apparatus is improved when using more rails. The use of several base members also has the advantage that several medical instruments can be fixed at the same time at different positions on the patient.

It will be understood that the above-mentioned features and those to be discussed below are applicable not only in the given combinations, but may also be used in other combinations or taken alone without departing from the scope of the present invention.

BRIEF DESCRIPTION OF THE DRAWINGS

Embodiments of the invention are illustrated in the drawings and will be described in more detail in the following description.

DETAILED DESCRIPTION OF PREFERRED EMBODIMENTS

Figure 1:
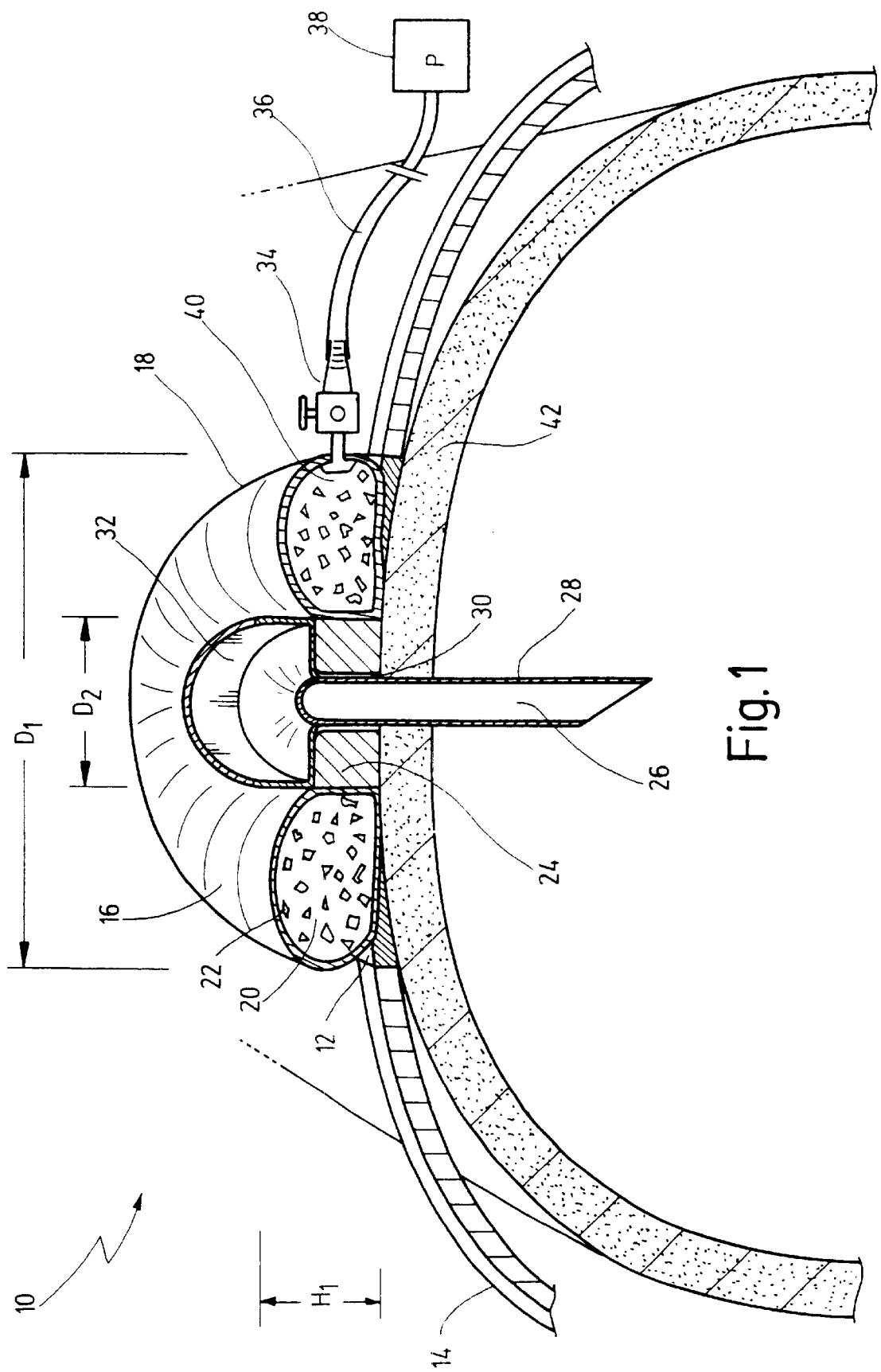
FIG. 1 shows a partially cross-sectional, perspective illustration of a first embodiment of the present invention.

A holding apparatus according to the present invention is shown in FIG. 1 and designated generally with the numeral 10. The holding apparatus 10 comprises a base member 12 secured to a rail 14 of a support frame shown only partially here. The base member 12 in the present case is a support ring to which a torus-shaped connecting member 16 is secured. The connecting member 16 can be adhered to the base member 12 or screwed thereto. In the present example, the connecting member 16 however is clamped to the base member 12 and thus can also be removed. In a further alternative embodiment, the base member 12 can be integrated into the connecting member 16. In this case, the base member 12 consists substantially of a stiffened underside of the connecting member 16.

The connecting member 16 comprises an elastic casing 18, which in the present case is made of silicone. The casing 18 is filled with a particulate material 20 whose particles 22 have a surface with substantially flat portions and edges. Thus, the individual particles 22 catch with one another very well when they are compressed.

The torus-shaped casing 18 filled with the particles 22 surrounds an annular retainer 24 whose outer circumference is adhered to the casing. The retainer 24 consists of a material which is hard compared to the casing 18, for example plastic, and alternatively to the embodiment shown here can also be formed to be hollow or to have channels.

A schematically illustrated trocar sleeve is designated with the numeral 26. The trocar sleeve 26 has a tubular shaft 28, which in the illustrated position is passed through the ring opening 30 of the retainer 24 and which expands to a hollow cylindrical valve housing 32 at its upper end.

Valve housing 32 of the trocar sleeve 26 normally has a valve flap for closing the shaft 28 and can also have a clamping device and/or one or more connectors. Such configurations of trocars or trocar sleeves are however known per se in the art and are not illustrated here for reasons of clarity.

An aerating and ventilating valve is designated with the numeral 34, which is connected to a pump 38 by a line 36. The valve 34 joins into the casing 18 of the connecting member 16 and has a sieve 40 whose mesh size is designed such that the particles 22 do not exit from the casing 18.

Air or an arbitrary gas can be pumped into or suctioned off of the casing 18 of the connecting member 16 through the valve 34 by the pump 38. The latter has the effect that a vacuum is generated in the casing 18, which causes the casing 18 to collapse. The consequence is that the individual particles 22 of the material 20 lose their freedom of movement and are pressed together. This in turn has the result that the otherwise flexible connecting member 16 is then "fixed" in its given form. Since the rigid mass surrounds the retainer 24, the rigid mass holds the retainer 24 in a certain orientation. The original freedom of movement of the particles 22 and thus the original flexibility of the connecting member 16 is returned when aerating the casing 18.

The abdominal wall of a patient to be treated is indicated with the numeral 42, through which the shaft 28 of the trocar sleeve 26 has been penetrated. The trocar sleeve 26 is thus tiltable about a so-called invariable point, which lies within the abdominal wall 42, assuming that the apparatus 10 is in its first flexible operational state.

The dimensions of the connecting member 16 are indicated with the parameters $D_1$, $D_2$ and $H_1$ and in the present case have the approximate values of $D_1=100$ mm, $D_2=30$ mm and $H_1=20$ mm.

As an alternative to the present embodiment, where a particulate material 20 is used within the casing 18 and the rigidity of the connecting member 16 can be changed with the valve 34 and the pump 38, the casing 18 can also be filled with a fluid whose viscosity is adjustable between being elastic and firm.

Preferably, the fluid is adjustable by applying an electric and/or magnetic signal. In this case, an electric connection or a magnetic coupling (not shown) is provided in place of the valve 34 and a corresponding field generator is necessary instead of the pump 38. The casing 18 as well as its connection to the retainer 24 however can be realized in the same manner as shown in FIG. 1.

The same also holds when a material is used for the material 20 which is flexible at a first adjustable operational temperature and is rigid at a second operational temperature. Corresponding means are required in this case, in place of the valve 34 and the pump 38 with which the temperature of the material can be changed as rapidly as possible. This can be a combined heating and cooling unit and the material is selected such that a distinct melting point is present in the region just above room temperature.

Figure 2:
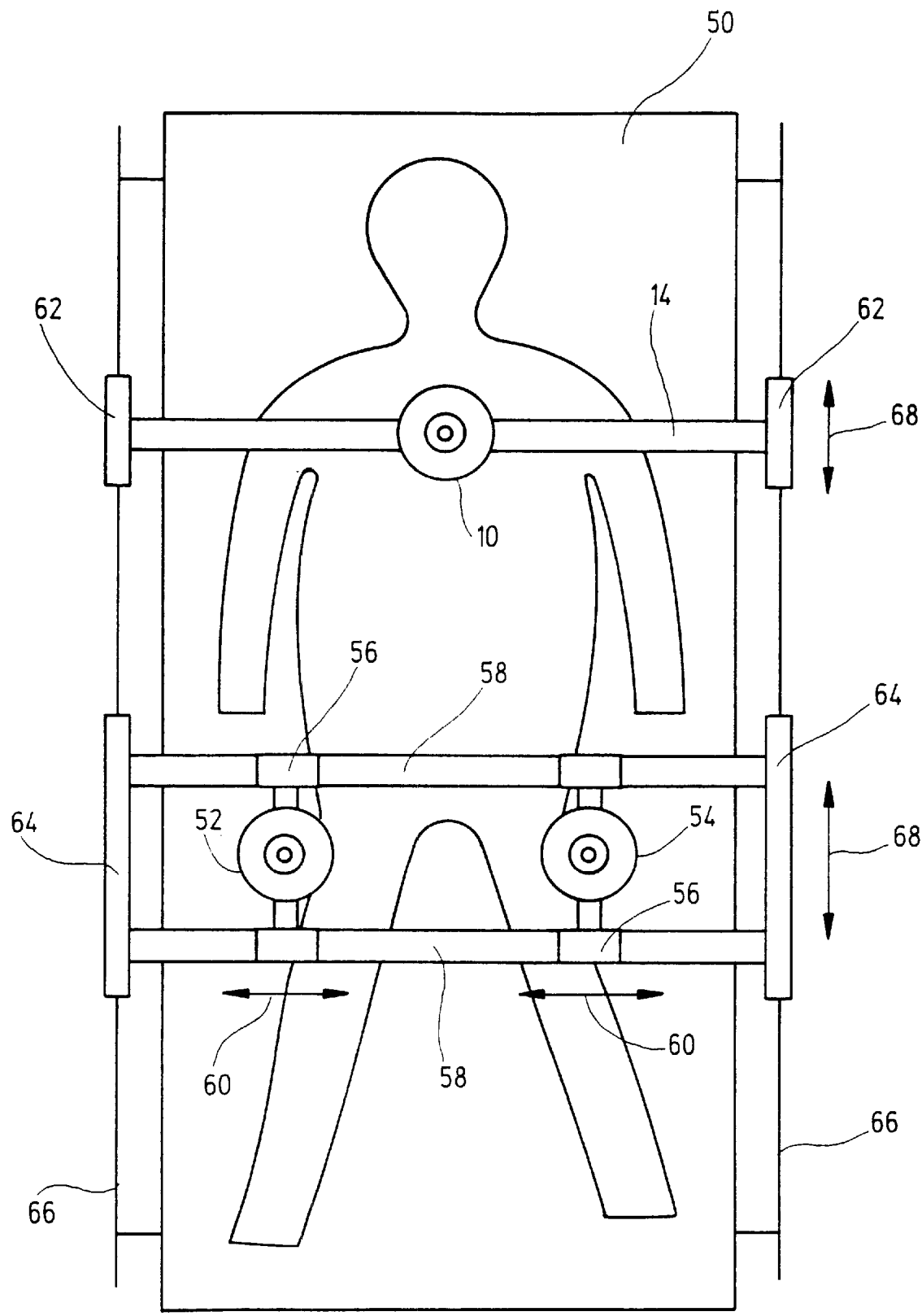
FIG. 2 shows an operating table from above with several holding apparatus according to the present invention.

An operating table 50 in FIG. 2 is equipped for example with a total of 3 holding apparatus 10 and 52, 54 according to the present invention. It will be understood that an operating table can also be provided with only one or any other number of holding apparatus 10.

The holding apparatus 10 is secured with its base member 12 on the rail 14 of the support frame mentioned in conjunction with FIG. 1. The holding apparatus 52, 54 in contrast are secured to a bracket 56, which is slidably mounted on two rails 58 in the direction of the arrow 60. Furthermore, it is possible to dispose the apparatus 52, 54 along the width of the operating table in a desired position due to the shiftability of the holding apparatus 52, 54 in the direction of the arrow 60.

The rail 14 as well as the two rails 58 are coupled via slide elements 62, 64 to slide rails 66, which are secured to both sides of the operating table 50 in longitudinal direction. Due to the slide elements 62, 64, it is possible to shift the rail 14 or the arrangement of the two rails 58 in longitudinal direction of the operating table 50, i.e. in the direction of the arrows 68. The slide elements 62, 64 can be rollers or other glide means and additionally be provided with adjustment means (not shown).

Figure 3:
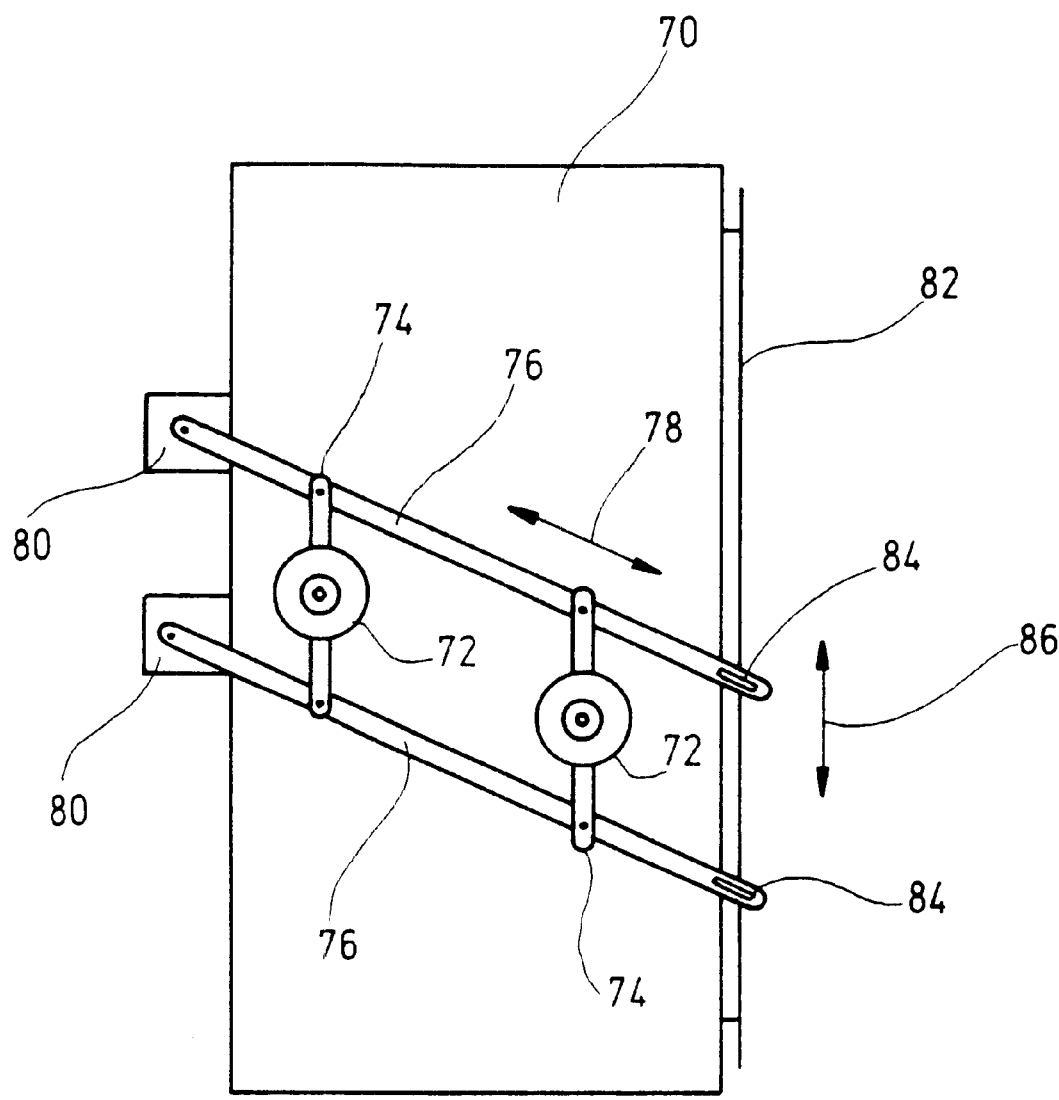
FIG. 3 shows an alternative configuration of an operating table with holding apparatus according to the present invention.

An operating table in FIG. 3 is designated with the numeral 70. The present holding apparatus 72 are again secured with brackets 74 slidably mounted on rails 76 in the direction of the arrow 78. In contrast to the previous embodiment, the two rails 76 however are mounted with one end rotatable or pivotal on plates 80. The other end of the rails 76 is connected to a slide rail 82 by pins, not shown in more detail. The pins are disposed in a slotted hole 84 of each rail 76, so that a compensation for length is made during rotation. The slide rail 82 in turn is secured to a longitudinal side of the operating table 70. It is also possible with this arrangement to adjust the present apparatus 72 in longitudinal direction of the operating table 70, i.e. in the direction of the arrow 86.

The operation of the present apparatus will be described in conjunction with FIGS. 4 and 5. The same reference numerals are used for the same elements already discussed in conjunction with the above figures.

A medical instrument is designated with the numeral 90 which is passed through the trocar sleeve 26 into the body 92 of a patient to be treated. The medical instrument in the present case is a grasping forceps.

Figure 4:
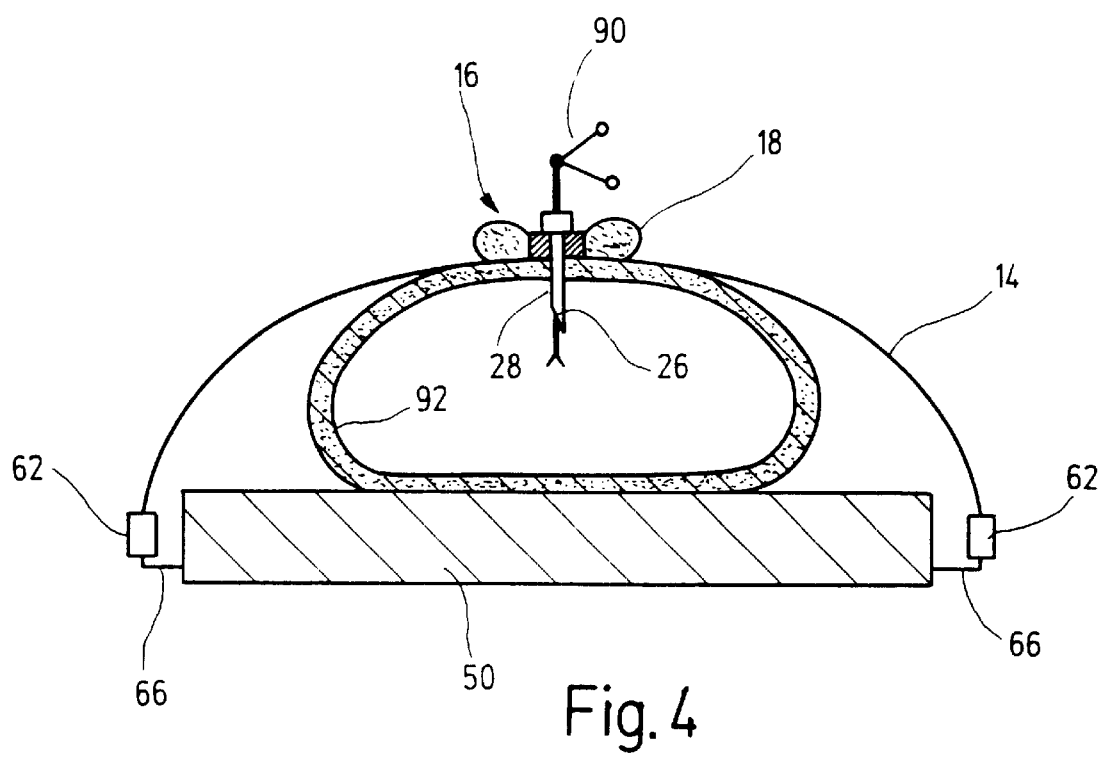
FIG. 4 shows the use of the present holding apparatus in cross-sectional view, where a medical instrument is fixed in a first position.
Figure 5:
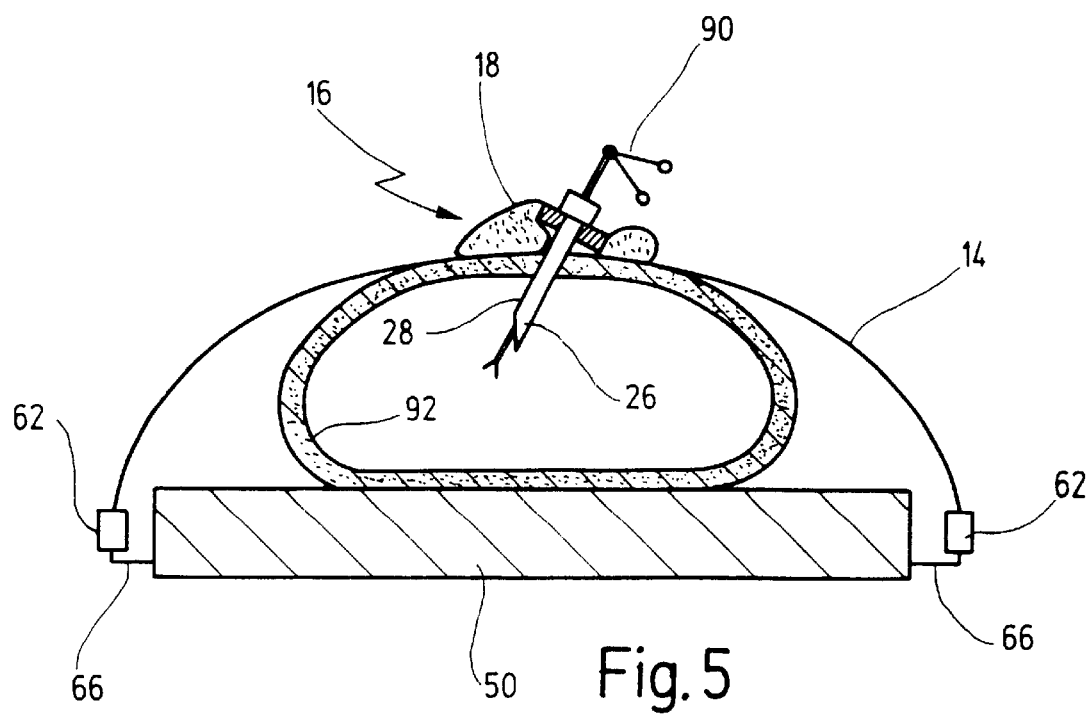
FIG. 5 shows the use of the present holding apparatus corresponding to FIG. 4, where the medical instrument is fixed in a second position inclined in comparison to the first position.

The trocar sleeve 26 in FIG. 4 is located approximately in the same position as shown in FIG. 1. The shaft 28 of the trocar sleeve 26 is disposed substantially perpendicular. This orientation however is often not suitable to reach the desired location within the body 92 of the patient. Moreover, the medical instrument 90 must frequently be inclined when passing through the incision in the body 92 of the patient to reach a certain organ.

For this purpose, the present apparatus at the beginning of the treatment is placed in a desired position relative to the patient with the aid of the rails 14, 58 or 76. The necessary incision into the body 92 of the patient is then made with the trocar, where the trocar sleeve 26 then remains in the patient's body 92 and can be oriented in the desired direction and angular position. The latter can be accomplished for example with the aid of an optical instrument, which in such cases is passed through the trocar sleeve 26.

When finding the proper position, the connecting member 16 is in its first flexible operational state. When using the embodiment of FIG. 1, this means that the casing 18 is filled with air, so that the particles 22 of the material 20 within the casing 18 can shift. In this operational state, the trocar sleeve 26 along with the retainer 24 can be tilted relative to the base 12, which causes the torus-shaped connecting member 16 to deform.

When the desired position is found, air is suctioned out of the casing 18 via the valve 34 by the pump 38, where a vacuum then arises in the casing 18. The connecting member 16 then is in its second rigid operational state and its last assumed form is fixed. At the same time, the retainer 24 and the trocar sleeve 26 are also fixed in the adjusted orientation. This condition is shown for example in FIG. 5.

Figure 6:
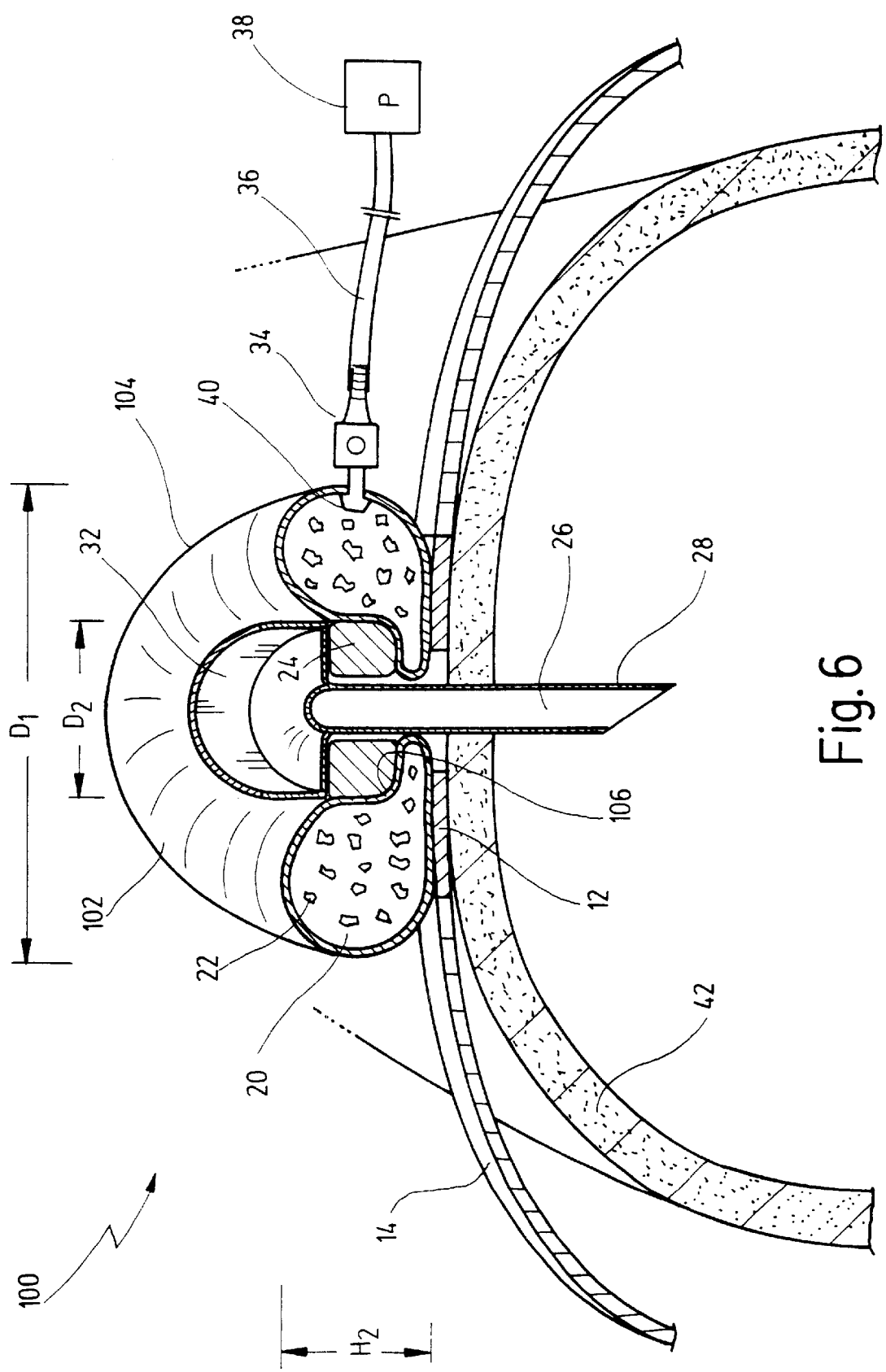
FIG. 6 shows a second embodiment of the present holding apparatus in a partially cross-sectional, perspective view.

A second embodiment of the present holding apparatus is designated in FIG. 6 generally with the numeral 100. The same reference numerals again are used for the same elements discussed above in the previous figures.

The apparatus 100 differs from the apparatus 10 in FIG. 1 essentially in that the connecting member 102 has a casing 104 which passes under the retainer 24, so that the retainer is nearly completely embedded in the casing 104. Furthermore, the edges 106 of the retainer 24 are distinctly rounded to avoid damaging the casing 104 when changing the position of the trocar sleeve 26. The stability of the trocar sleeve 26 is enhanced, especially when it is strongly inclined in one direction, due to the underside support of the retainer 24 with the casing 104 and the material 20 contained in the casing.

In a further embodiment, not illustrated here, the retainer 24 can be integrated into the casing 104. In this case, the head 32 of the trocar sleeve 26 then lies directly on the casing 104.

What is claimed is:

1. An apparatus for holding a trocar sleeve in different spatial orientations relative to a patient, comprising:
    a base member which can be positioned and fixed relative to the patient,
    a retainer for receiving and holding a trocar sleeve inserted into said body of said patient, and
    a connecting member for connecting said base member to said retainer, wherein said connecting member has a first operational state in which it is flexible, allowing said retainer to tilt with respect to said base member, and has a second operational state in which it is rigid, and
wherein said connecting member comprises an elastic casing filled with a material being variable in rigidity.

2. The apparatus of claim 1, wherein said material is a particulate material having a plurality of particles, and said apparatus further comprises means for generating a vacuum in said casing.

3. The apparatus of claim 2, wherein a surface of said particles comprises substantially flat portions and edges such that said particles are prevented from passing by one another in a compressed state, thereby forming a rigid mass in said second rigid operational state of said connecting member.

4. The apparatus of claim 1, wherein said material is a fluid whose viscosity is adjustable between being elastic and being rigid.

5. The apparatus of claim 4, wherein said viscosity of said material is adjustable through an electric signal.

6. The apparatus of claim 4, wherein said viscosity of said material is adjustable by a magnetic signal.

7. The apparatus of claim 1, wherein said base member is secured to a support frame, and wherein said frame can be adjustably and fixedly mounted to an operating table.

8. The apparatus of claim 7, wherein said support frame comprises at least one rail arranged over said operating table.

9. The apparatus of claim 8, wherein said base member is slidably secured to said one rail.

10. The apparatus of claim 9, wherein said at least one rail is shiftable along said operating table.

11. The apparatus of claim 1, wherein said base member is secured to a support frame which can be adjustably and fixedly mounted to an operating table, said support frame comprising at least one rail, said at least one rail being mounted to said operating table to be pivotable about a pivot point.

12. The apparatus of claim 1, further comprising a plurality of said base members and a support frame comprising several rails, wherein said plurality of said base members are secured to said rails.

13. The apparatus of claim 12, wherein said rails extend in a proximately transverse direction with respect to a longitudinal axis of said patient.

14. An apparatus for holding a trocar sleeve in different spatial orientations relative to a patient, comprising:
- a base member which can be positioned and fixed relative to the patient,
- a retainer for receiving and holding a trocar sleeve inserted into said body of said patient, and
- a connecting member for connecting said base member to said retainer, wherein said connecting member has a first operational state in which it is flexible, allowing said retainer to tilt with respect to said base member, and has a second operational state in which it is rigid, and wherein said connecting member comprises a material which is flexible at an adjustable first operational temperature in said first operational state of said connecting member and is rigid at a second operational temperature in said second operational state.

15. An apparatus for holding a trocar sleeve in different spatial orientations relative to a patient, comprising:
- a base member which can be positioned and fixed relative to the patient,
- a retainer for receiving and holding a trocar sleeve inserted into said body of said patient, and
- a connecting member for connecting said base member to said retainer, wherein said connecting member has a first operational state in which it is flexible, allowing said retainer to tilt with respect to said base member, and has a second operational state in which it is rigid, and wherein said connecting member is a torus-shaped body having a central opening, said retainer being arranged in said opening.

16. The apparatus of claim 15, wherein said base member is secured to a support frame, and wherein said frame can be adjustably and fixedly mounted to an operating table.

17. The apparatus of claim 16, wherein said support frame comprises at least one rail arranged over said operating table.

18. The apparatus of claim 17, wherein said base member is slidably secured to said one rail.

19. The apparatus of claim 18, wherein said at least one rail is shiftable along said operating table.

20. The apparatus of claim 15, wherein said base member is secured to a support frame which can be adjustably and fixedly mounted to an operating table, said support frame comprising at least one rail, said at least one rail being mounted to said operating table to be pivotable about a pivot point.

21. The apparatus of claim 15, further comprising a plurality of said base members and a support frame comprising several rails, wherein said plurality of said base members are secured to said rails.

22. The apparatus of claim 21, wherein said rails extend in a proximately transverse direction with respect to a longitudinal axis of said patient.

* * * * *